(12) United States Patent
Lualdi

(10) Patent No.: US 11,723,671 B2
(45) Date of Patent: Aug. 15, 2023

(54) SURGICAL BIT AND PRODUCTION METHOD

(71) Applicant: HPF S.R.L., Fagagna (IT)

(72) Inventor: Gabriele Lualdi, Fagagna (IT)

(73) Assignee: HPF S.R.L., Fagagna (IT)

( * ) Notice: Subject to any disclaimer, the term of this patent is extended or adjusted under 35 U.S.C. 154(b) by 170 days.

(21) Appl. No.: 17/088,985

(22) Filed: Nov. 4, 2020

(65) Prior Publication Data

US 2021/0128175 A1 May 6, 2021

(30) Foreign Application Priority Data

Nov. 4, 2019 (IT) .................. 102019000020274

(51) Int. Cl.
*A61B 17/16* (2006.01)
*B33Y 80/00* (2015.01)

(52) U.S. Cl.
CPC ...... *A61B 17/1617* (2013.01); *A61B 17/1631* (2013.01); *B33Y 80/00* (2014.12)

(58) Field of Classification Search
CPC . A61B 17/16; A61B 17/1613; A61B 17/1615; A61B 17/1617; A61B 17/162; A61B 17/1631; A61B 17/1642
See application file for complete search history.

(56) References Cited

U.S. PATENT DOCUMENTS

| | | | | |
|---|---|---|---|---|
| 6,053,922 A * | 4/2000 | Krause | ................ | A61B 17/164 606/180 |
| 8,117,950 B2 * | 2/2012 | Kozak | ................ | B25B 23/0014 81/177.75 |
| 8,821,494 B2 * | 9/2014 | Pilgeram | ........... | A61B 17/0482 606/80 |
| 9,381,031 B2 * | 7/2016 | Rains | ................... | A61B 17/164 |
| 10,022,131 B1 * | 7/2018 | Burley | ............... | A61B 17/1631 |
| 10,569,396 B2 * | 2/2020 | Krause | ............... | A61B 17/1631 |
| 10,582,935 B2 * | 3/2020 | Burley | ............... | A61B 17/1615 |
| 10,631,879 B2 * | 4/2020 | Omohundro | ....... | A61B 17/1633 |
| 10,702,289 B2 * | 7/2020 | Saw | .................. | A61B 17/1675 |
| 10,856,889 B1 * | 12/2020 | Burley | ............... | A61B 17/1664 |
| 11,022,169 B2 * | 6/2021 | Omohundro | ............. | F16C 1/06 |
| 2008/0188854 A1 * | 8/2008 | Moser | ................ | A61B 17/1631 606/80 |
| 2010/0152739 A1 * | 6/2010 | Sidebotham | ....... | A61B 17/1631 29/428 |
| 2011/0015675 A1 * | 1/2011 | Howard | ............ | A61B 17/0401 606/232 |
| 2011/0152867 A1 * | 6/2011 | Petrzelka | ............. | A61B 17/808 227/175.1 |
| 2013/0261628 A1 * | 10/2013 | Burley | ............... | A61B 17/1615 606/80 |
| 2013/0296864 A1 * | 11/2013 | Burley | ................... | A61B 17/17 606/80 |
| 2017/0056979 A1 * | 3/2017 | Krause | ............... | A61B 17/1631 |

(Continued)

FOREIGN PATENT DOCUMENTS

| | | | | |
|---|---|---|---|---|
| EP | 3815631 A1 | * | 5/2021 | ......... A61B 17/1617 |
| NL | 8204763 A | * | 7/1984 | ............. B25B 27/10 |
| WO | WO-2014107729 A2 | * | 7/2014 | ......... A61B 17/1631 |

*Primary Examiner* — Eric S Gibson

(74) *Attorney, Agent, or Firm* — BakerHostetler

(57) ABSTRACT

The invention concerns a surgical drill bit able to be connected to a surgical tool, comprising a flexible stem. The invention also concerns a corresponding method to produce the surgical drill bit.

11 Claims, 4 Drawing Sheets

(56) References Cited

U.S. PATENT DOCUMENTS

| | | | | |
|---|---|---|---|---|
| 2017/0333052 A1* | 11/2017 | Ding | ............ | A61B 17/1671 |
| 2018/0065235 A1* | 3/2018 | Krause | ............ | B23B 45/005 |
| 2018/0084985 A1* | 3/2018 | Saw | ............ | A61B 17/1631 |
| 2018/0258979 A1* | 9/2018 | Omohundro | ............ | F16C 1/08 |
| 2021/0128175 A1* | 5/2021 | Lualdi | ............ | A61B 17/1631 |

* cited by examiner

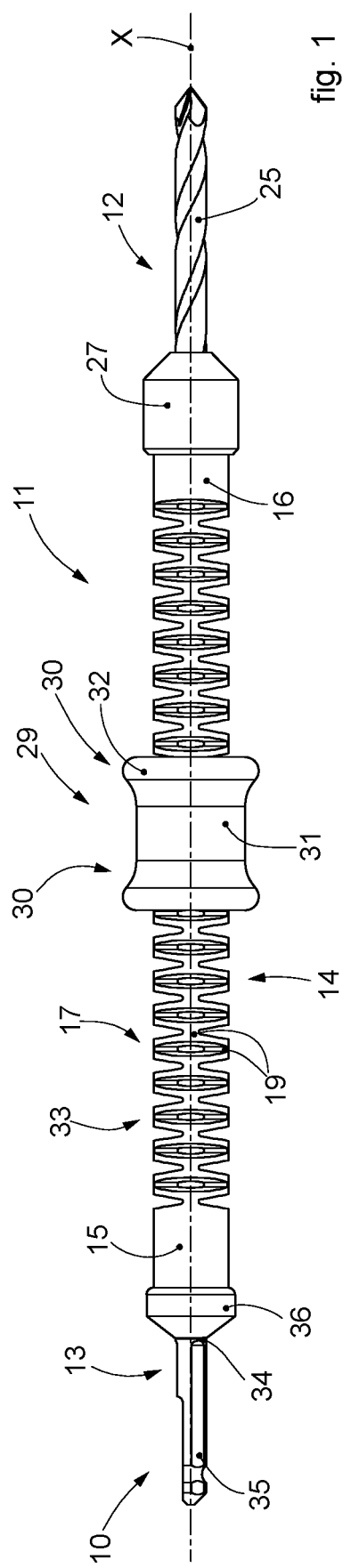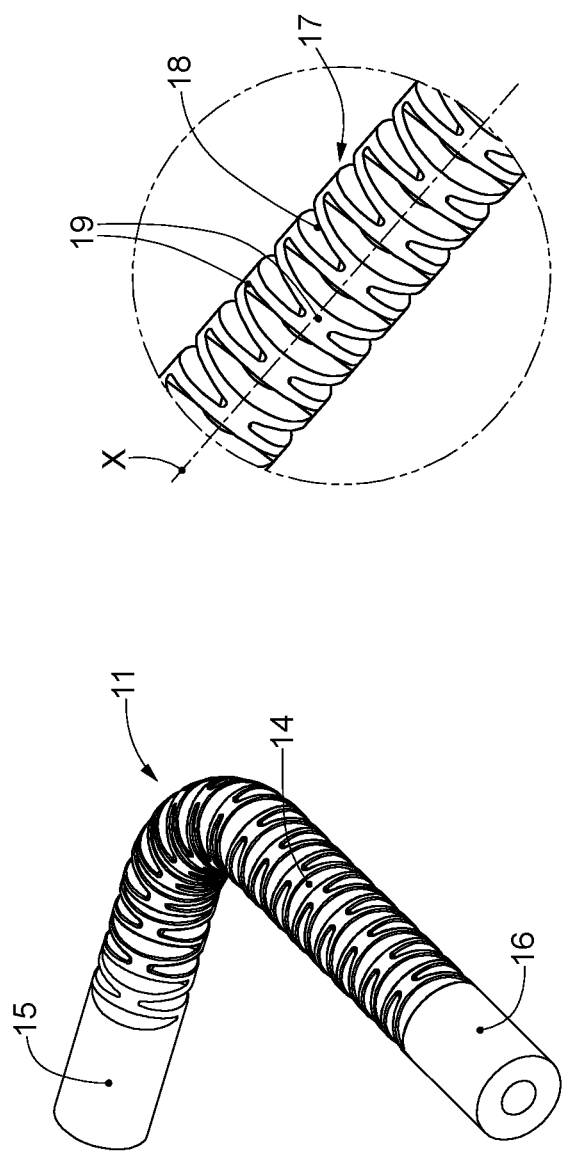

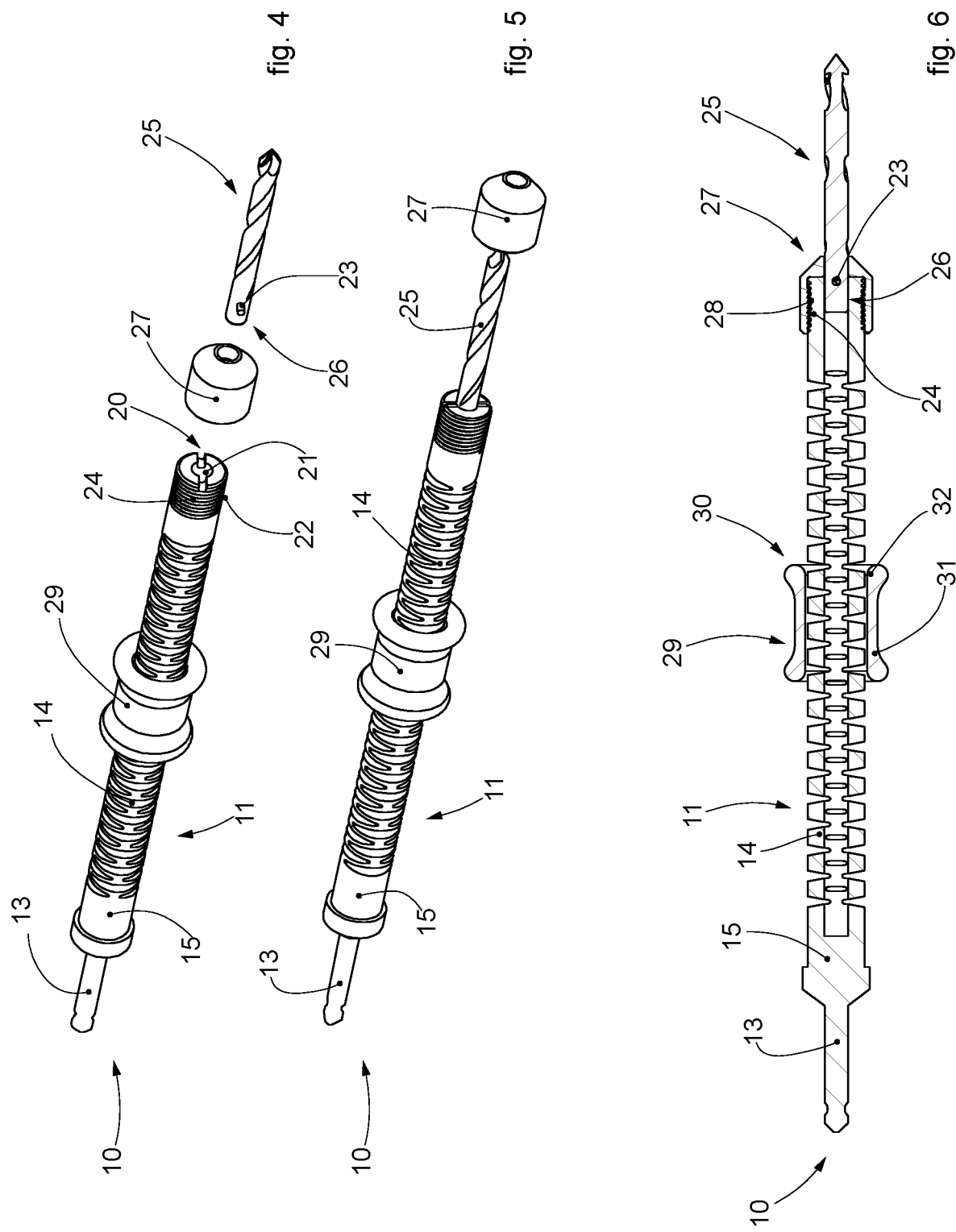

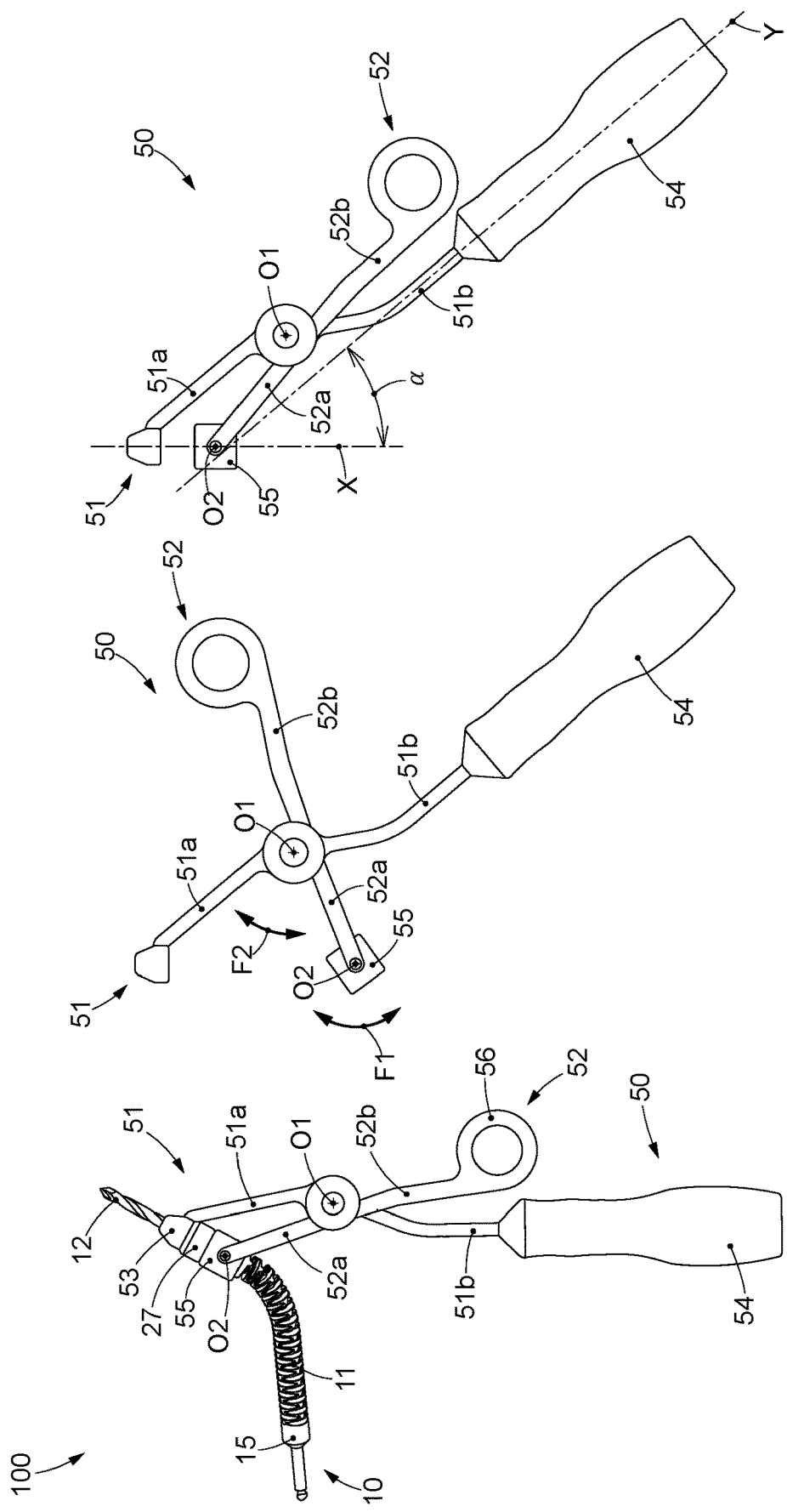

SURGICAL BIT AND PRODUCTION METHOD

FIELD OF THE INVENTION

Embodiments described here concern a surgical drill bit and the method to produce it.

The drill bit in question is suitable for use with surgical tools or devices, such as drills, screwdrivers, cutters and similar tools or devices that involve the use of a drill bit. For example, the drill bit can be used in the field of prosthetic surgery, for example in the field of orthopedics or dentistry.

BACKGROUND OF THE INVENTION

In the medical/surgical field, for example for orthopedic prostheses, it is known to use tools, such as drills, screwdrivers, cutters and suchlike, for interventions on human or animal bone tissues, for example in spinal surgery, orthopedic and trauma surgery, in odontostomatological surgery, in prosthetic surgery, in veterinary surgery and suchlike.

The tools known in the state of the art comprise a tool body and a mandrel, by means of which a drill bit is attached to the tool body and which transmits the rotational motion to the drill bit.

It is also known, in general, that there are cases in which the work zone in which the surgeon has to intervene is difficult to reach, for example due to lack of maneuvering space due to the presence of obstacles.

In these cases, articulated mechanical shafts are known, which are applied to the tool and are angularly orientable in order to position the drill bit in the work zone with the necessary angle of incidence.

Such articulated shafts are usually interposed between the mandrel and the drill bit, transmitting the rotational motion from the mandrel to the drill bit.

Articulated shafts usually have a stem, comprising at least in one part of it elements that are constrained to each other but partly movable, such as articulated mechanical links, cardan joints or suchlike, able to ensure flexibility to the stem, and two ends, respectively for inserting the drill bit and for inserting the flexible shaft on the mandrel.

In general, known articulated shafts are usually made of metal material, such as stainless steel for example.

Composite articulated shafts are also known, for example made of metal material associated with a sheath or coating made of polymeric material, such as silicone, usually used to cover at least a part of the articulated shaft, allowing to protect the hands while gripping the shaft in order to direct the drill bit.

US 2011/0152867 A1 describes an articulated instrument comprising an external structure. The articulated instrument comprises, inside the external structure, a shaft, flexible in at least one portion thereof and able to cooperate with interchangeable drill bits. The articulated instrument can assume at least two extreme positions by moving an articulated head of the external structure connected to the distal end by an articulated joint.

US 2001/001588 A1 describes a boring instrument comprising a drill head mounted on a flexible shaft. The connection of the drill head to the flexible shaft can be of a known type, preferably such that the drill head is removable. The flexible shaft, at least in one part, has a spiral shape and comprises a through hole for the passage of a guide wire.

In some applications, the drill bit and the articulated shaft are subjected to stresses, even critical ones, when for example the working angle is particularly unfavorable or the twisting torque that has to be applied to carry out the working is particularly high. For example, a drill bit may not be sharp enough, because it is worn, and may require more thrust to perform the working, or the cutting angles may not be optimal with respect to the work surface.

From U.S. Pat. No. 9,381,031 B2, an instrument is also known for making a cavity in an intra-medullary canal of a bone, which comprises a flexible shaft, an expandable cutting element and a distal section comprising a drill bit able to form an entry channel through the cortical bone. The expandable cutting element can be coupled with the flexible shaft directly or indirectly. In turn, the drill bit can be coupled with the expandable cutting element directly or indirectly. The flexibility of the shaft is due to the modulus of elasticity of the material and the reduced diameter of its section. The expandable cutting part has a plurality of flexible helical cutting arms, which can be compressed in order to excavate the inside of the canal without damaging the cortical wall.

US 2005/0043739 describes a flexible shaft made of rigid material, the flexibility of which depends on the low ratio between the moment of inertia of the section calculated with respect to an axis perpendicular to the longitudinal axis of the shaft and the longitudinal axis itself. A cutting end can be connected to the shaft in a removable way by means of an attachment element.

US 2012/0203231 instead describes a method to carry out surgical micro-drilling using a drilling tool that comprises a flexible shaft and a drill head, welded or otherwise secured to the flexible shaft. The flexible shaft can be made by means of a solid tube on which a series of cuts are made, passing through, or not, the entire thickness of the shaft, or by a coil wound with a spiral configuration.

One disadvantage of the solutions known in the state of the art is that it can be difficult to control the twisting torque that is applied to the drill bit.

For example, in use and with critical stresses, the drill bit can get stuck or break inside the bone tissue while working.

This can happen, for example, due to the excessive twisting torque applied when the cutting action of the drill bit is not able to perform the working effectively.

In the worst cases the drill bit can break and the broken stump is left, by necessity, inside the bone tissue, because it is difficult or impossible to extract.

Furthermore, it can be difficult to apply the twisting torque in the working direction.

In fact, part of the torque provided by the tool can be dispersed or not exploited for example due to contact and rubbing of the rotating drill bit with a possible drill bit-guide tool associated with it, and used to keep the drill bit in the work zone.

Another disadvantage of articulated shafts for medical-surgical applications as above is that they usually have a limited possibility of orientation and angular adjustment.

Another disadvantage is that the presence of the articulated shaft, in consideration of its structure and the material of which it is made, causes an encumbrance and an increase in the overall weight of the tool. In this way, in the long run, the operator can get tired and, in general operating comfort decreases.

Another disadvantage is the difficulty of sanitization, in particular sterilization. In fact, known articulated shafts must be subjected to sanitization in order to be reused, for example by sterilization, in the autoclave or with hydrogen peroxide vapors.

Impurities such as organic material, such as for example fragments of bone, cartilage, blood or other organic tissue, or inorganic material, can infiltrate the components of the articulated shafts, making sanitization ineffective.

The solutions in which the external sheath is provided which covers part of the articulated metal shaft also have the disadvantage of being difficult to sterilize, since impurities can infiltrate between the sheath and the shaft body, for example in the case where the sheath is worn and cracks or micro-cracks are formed.

Another disadvantage of known solutions are the costs associated with said sanitization, necessitated by the fact that known drill bits and articulated shafts are reused, in terms of use of dedicated instrumentation and materials, of personnel employed and of management costs.

There is also a need to reduce the costs of drill bits and articulated shafts.

Finally, a disadvantage of known solutions is that they require a plurality of operations for the assembly and disassembly of the articulated shaft and the drill bit from the tool.

There is therefore a need to perfect a surgical drill bit that can overcome at least one of the disadvantages of the state of the art.

In particular, one purpose of the present invention is to provide a drill bit that allows the torque transmitted from the tool to the drill bit to be controlled in a suitable manner.

In particular, one purpose of the present invention is to provide a drill bit that can be directed and oriented in space easily, in order to obtain the desired working direction.

Another purpose of the present invention is to provide a drill bit that does not block or break inside the material in which the hole is being made.

Another purpose is to provide a drill bit that has an articulation capacity and preferably a greater flexibility than that of currently known solutions.

Another purpose is to reduce the overall weight of the tool as much as possible when equipped with said drill bit.

Another purpose is to make a drill bit that is disposable and therefore, since it is not reused, does not need to be sanitized.

Another purpose is to provide a drill bit that makes the operations to assemble it on the tool, and to disassemble it therefrom, easy and quick.

Another purpose is to provide a drill bit that allows to reduce operations and management costs, in particular for sanitization.

Another purpose is to reduce production costs compared with current solutions.

Another purpose is to perfect a method to make a surgical drill bit that is economical, versatile and quick.

The Applicant has studied, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the present invention or variants to the main inventive idea.

In accordance with the above purposes, some embodiments described here concern a surgical drill bit and the method to produce it, which overcome the limits of the state of the art and eliminate the defects present therein.

The invention in question is suitable for use with surgical tools or devices, such as drills, screwdrivers, cutters and suchlike, for interventions on human or animal bone tissues, for example in spinal surgery, orthopedic and trauma surgery operations, in odontostomatological surgery, in prosthetic surgery, in veterinary surgery and suchlike.

According to some embodiments, the drill bit as above is able to be connected to the surgical tool or device, for example by means of a mandrel.

According to the invention, the drill bit comprises a flexible stem, completely made of polymeric material, which develops along a central axis of development.

One advantage is the possibility of making the drill bit with low cost materials, reducing the production costs of the drill bit.

According to the invention, the flexible stem is provided with a proximal part, to which a pointed end is directly coupled.

According to the invention, the flexible stem is also provided with a distal part which has an attachment for the rotational connection to said tool.

The attachment can be able to allow the connection of the drill bit onto the tool.

One advantage of the invention is therefore that it allows the direct connection of the drill bit to the tool without the interposition of a separate articulated shaft, simplifying the assembly of the drill bit even when an angular orientation thereof is required.

According to some embodiments, the flexible stem has, in a flexible central part thereof, a three-dimensional reticular structure with meshes of polymeric material.

One advantage of the reticular structure is that it is a light structure, which helps to reduce, as much as possible, the overall weight of the tool when equipped with the drill bit.

According to some embodiments, the reticular structure has a repetition in space of bilobed elements each connected to at least one contiguous bilobed element by means of at least two nodes.

Advantageously, such nodes are substantially angularly opposite each other with respect to the central axis of development, allowing to produce a symmetrical axial structure. It is therefore an advantage that there is no preferential orientation of use of the drill bit.

Such nodes can also develop along the central axis of development, in accordance with an angularly offset angular development, wherein the at least two nodes, that connect one bilobed element to at least one contiguous bilobed element, are angularly offset with respect to at least another two nodes, which connect another bilobed element to at least one contiguous bilobed element, along the central axis of development.

One advantage is that the reticular structure described above can guarantee sufficient strength to transmit, at the point of application, a twisting torque at least up to values of 5 Nm, corresponding to the torque values usually required in medical/surgical applications.

One advantage of this reticular structure is also the increase in the flexibility of the flexible stem, with a consequent improved capacity for orientation and adjustment in space. The stem in fact can be, for example, curved up to an angle of 180° with a radius of curvature in the curved part of less than 15 mm.

According to some embodiments, the nodes as above act as predetermined breaking points in correspondence with the flexible stem.

Advantageously, the polymeric material and the reticular structure with nodes substantially angularly opposite each other with respect to the central axis of development allow to create weak points in correspondence with the flexible stem. In this way it is possible to reduce the probability that the drill bit will remain blocked or break inside the bone tissue.

For example, it is possible to predetermine the breaking of such points in the presence of torques that exceed a minimum value, usually comprised between about 5 Nm and 6 Nm, beyond which the functionality of the tool is no longer guaranteed.

One advantage is therefore that these programmed breaking points allow to control the torque applied to the work point. During use, when the applied torque reaches the minimum value, the drill bit can snap at the programmed breaking points.

The drill bit, advantageously, comprises a gripping bushing, positioned around the flexible stem sliding along the central axis of development between the distal part and the proximal part of the flexible stem.

The bushing can help to better direct the pointed end in the work zone, allowing to not press excessively against a possible drill bit-guide, helping to better control the torque provided by the tool.

According to one realization variant, the drill bit can cooperate with a bushing comprised in a support and guide device. The support and guide device advantageously has two arms pivoted to each other at an intermediate point, one arm comprising at one end a manipulation handle and at the opposite end a drill bit-clamping element and the other arm comprising at one end a gripping element and at the opposite end the bushing.

Advantageously, the bushing is pivoted on the end of the arm and able to slide along the flexible stem of the drill bit.

The support and guide device can have a clamped position in which the bushing and the drill bit-clamping element cooperate with the drill bit, in order to keep it fixed with respect to the support and guide device.

Advantageously, in the clamped position the support and guide device can manipulate the drill bit. In this way it is possible to further improve the manipulation of the drill bit in the work zone. Some embodiments described here also concern a method to produce a surgical drill bit able to be connected to a surgical tool or device.

The method can provide to produce a flexible stem completely of polymeric material provided with a proximal part and with a distal part, wherein said distal part is made so as to define an attachment for the rotational connection to the tool, and to couple a pointed end to the proximal part.

One advantage is therefore the possibility of making the drill bit with low-cost materials.

According to some embodiments, the method to produce a surgical drill bit provides that the flexible stem is made by means of additive manufacturing technology, in particular by means of 3D rapid prototyping or injection molding.

Another advantage is therefore the possibility of making the drill bit by means of low-cost methods, further reducing the production costs of the drill bit.

The low production costs can therefore allow to use a flexible drill bit, which also comprises the functionality of known articulated shafts, in a disposable mode.

In this way the additional advantages of a drill bit that is always new, therefore with maximum cutting efficiency, and always clean are obtained, without resorting to the sterilization of the drill bit itself and of an articulated shaft.

Therefore all additional costs related to sanitation are eliminated at the same time reducing the risk associated with imperfect sanitation. Advantageously, the pointed end can be connected to the proximal part of the flexible stem in an irremovable manner. In this way, it is possible to obtain a better stability of the drill bit, the end of which cannot be detached, for example due to the vibrations that may occur during use. Furthermore, compared to removable drill bits, there is an advantage also in relation to the speed with which the instrument can be readily used by the surgeon or operator, since the pointed end as above is pre-assembled and irremovable and no additional operating times are required to connect the pointed end with the proximal part of the stem. Furthermore, as described above, the drill bit according to the present description is disposable and can be eliminated after use, including the pointed end connected in an irremovable manner, to the benefit of safety and sanitation.

BRIEF DESCRIPTION OF THE DRAWINGS

These and other aspects, characteristics and advantages of the present invention will become apparent from the following description of some embodiments, given as a non-restrictive example, with reference to the attached drawings wherein:

FIG. 1 is a front view of a surgical drill bit according to some embodiments described here;

FIG. 2 is a three-dimensional view of a flexible stem of the drill bit of FIG. 1, in a flexed position;

FIG. 3 is a three-dimensional detailed view of the flexible stem of FIG. 2;

FIG. 4 is an exploded three-dimensional view of the drill bit of FIG. 1;

FIG. 5 is an exploded three-dimensional view of an assembly step of the drill bit of FIG. 1;

FIG. 6 is a section front view of the drill bit of FIG. 1;

FIG. 10 is a three-dimensional view of a surgical assembly during use in which the drill bit of FIG. 1 is in a flexed or bent configuration;

FIGS. 11-12 are front views of a support and guide device for a surgical drill bit according to some embodiments described here.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 9:
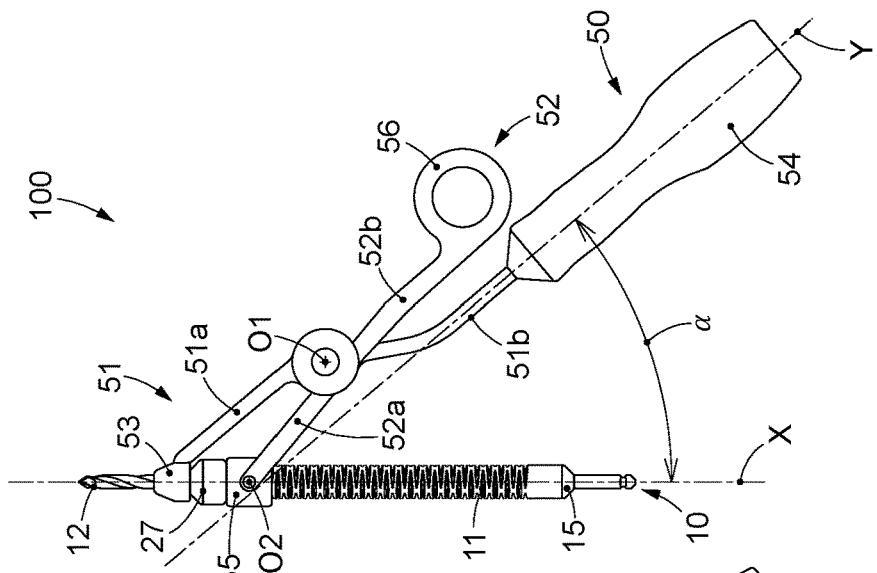
FIGS. 7-9 are front views of a surgical assembly according to some embodiments described here.

We will now refer in detail to the possible embodiments of the invention, of which one or more examples are shown in the attached drawings. Each example is supplied by way of illustration of the invention and shall not be understood as a limitation thereof. For example, one or more characteristics shown or described, insomuch as they are part of one embodiment, can be varied or adopted on, or in association with, other embodiments to produce other embodiments. It is understood that the present invention shall include all such modifications and variants.

With reference to the attached drawings, a surgical drill bit 10 is described, suitable for use with surgical tools or devices such as drills, screwdrivers, cutters and suchlike.

According to some embodiments, the drill bit 10 is able to be connected to a surgical tool or device.

For example, the connection can occur by means of a mandrel.

According to the invention, the drill bit 10 comprises a flexible stem 11 completely made of polymeric material. For example, the polymeric material is preferably polyamide, but it can also be polyethylene, polypropylene or suchlike.

According to the invention, the flexible stem 11 is provided with a proximal part to which a pointed end 12 is directly coupled and a distal part which has an attachment 13 for the rotational connection to the tool.

According to some embodiments, the pointed end 12 can be connected to said proximal part of said flexible stem 11 in an irremovable manner.

According to some embodiments, the flexible stem 11 develops along a central axis of development X.

According to some embodiments, the flexible stem 11 also comprises, in a single body, a flexible central part 14, disposed between the distal part and the proximal part. In particular, the flexible central part 14, the distal part and the proximal part can be formed in a single body.

The distal part can comprise an attachment end 15 which has the attachment 13.

According to some embodiments, the attachment end 15 can have a projecting attachment 13, such as a tang or suchlike.

According to some variants, the attachment can be configured inversely with respect to the previous configuration, presenting a seating suitable to cooperate with a projecting element disposed on the tool.

The proximal part can have a connection end 16 to which the pointed end 12 is coupled.

According to some embodiments, the flexible central part 14 has a three-dimensional reticular structure 33 with meshes of polymeric material.

The reticular structure 33 can consist of a repetition in space of meshes formed by bilobed elements 17.

Each bilobed element 17 can be connected to at least one contiguous bilobed element 17 by means of at least two nodes 19.

According to some embodiments, the nodes 19 that connect each bilobed element 17 to the at least one contiguous bilobed element 17 are disposed substantially angularly opposite each other with respect to the central axis of development X.

According to some embodiments, the nodes 19 develop along the central axis of development X, according to an angularly offset angular development, wherein the at least two nodes 19 that connect one bilobed element 17 to at least one contiguous bilobed element 17 are angularly offset with respect to at least another two nodes 19 that connect another bilobed element 17 to at least one contiguous bilobed element 17 along the central axis of development X.

According to some embodiments, the angle by which the at least two nodes 19 are offset with respect to the other at least two nodes 19 can be comprised between 10° and 90°, advantageously between 45° and 90°, preferably 90°.

As the angle changes, there is a change in the compromise between lightness, which increases as the angle increases, and strength, which on the contrary decreases as the angle increases. Therefore, by varying the angle it is possible to design the programmed breaking points for the torque values required by the application.

With angles comprised between 45° and 90° it would be possible to obtain a greater lightness, with a sufficient strength for applications in which a high twisting torque is not required, during use.

Advantageously, an angle substantially of 90° could be able to give the flexible stem the overall minimum resistance value that can be reached by the structure as described. This value may correspond for example to a minimum value, usually comprised between about 5 Nm and 6 Nm, beyond which the tool no longer guarantees its functionality.

According to some embodiments, the bilobed elements 17 can be hollow in their central part.

Advantageously, the reticular structure 33 is also able to allow the drill bit 10 to compress longitudinally, in order to maintain the freedom of movement of the meshes.

According to some embodiments, the drill bit 10 has predetermined breaking points. For example, the flexible stem 11 can break in a predetermined manner in correspondence with the nodes 19 as above.

According to one variant, such breaking points can correspond to the attachment 13 to the mandrel. For example, the attachment 13 can break in a predetermined manner in correspondence with a connection point 34 between a coupling part 35 and a base 36 of the attachment 13.

Such breaking points can be designed based on the modulus of resistance to torsion of the material together with the mechanical structure of the flexible stem 11 and/or of the attachment 13.

According to some embodiments, the attachment 13 is able to allow the drill bit 10 to be fixed onto the tool, for example by means of the mandrel.

By way of example, the attachment 13 toward the mandrel can be an AO, Hudson, Zimmer or similar attachment.

According to some embodiments, the attachment 13 is made of polymeric material. For example, the polymeric material is preferably polyamide, but it can also be polyethylene, polypropylene or suchlike.

According to one realization variant, the attachment 13 is made of metal material.

With reference to FIG. 1, the attachment 13 can be in a single body with the attachment end 15.

According to one realization variant not shown, the attachment 13 can also be fixed to the attachment end 15, for example by means of screwing or interlocking.

According to some embodiments, the connection end 16 has a positioning mean 20 for positioning the pointed end 12.

For example and with reference to FIG. 4, the positioning mean 20 comprises a central hole 21.

For example and with reference to FIG. 4, the positioning mean 20 also comprises an attachment part 22 in which an attachment element 23 of the pointed end 12 is positioned.

According to some embodiments, the connection end 16 has a fixing mean 24 for fixing the pointed end 12.

For example and with reference to FIG. 6, the fixing mean 24 is a threaded portion. As a further example the fixing mean 24 can be an interlocking mean.

According to some embodiments, the pointed end 12 comprises a metal element 25, suitable to carry out the work on the bone tissue.

The metal element 25 can for example be made of surgical steel.

For example, the metal element 25 can be a sharp or pointed tool for perforating, or drilling, or for removing material, in particular bone tissue, in particular a surgical instrument drill bit, that is a sharp or pointed tool with a longitudinal development, for example with a shape similar to an Archimedes screw, such as a drill bit, or a cutter bit, which can have a pointed, or a conical, or a truncated cone shape, or suchlike. The metal element 25 can also be an element for smoothing and suchlike.

According to some embodiments, the metal element 25 has a tang 26. Such tang 26 is able to be connected with the connection element 16.

As indicated above, in some embodiments the pointed end 12 can be connected to the proximal part of the flexible stem 11 in an irremovable manner.

In particular, for this purpose, according to possible embodiments, the metal element 25 can be connected to the connection element 16 in an irreversible manner.

According to one possible implementation of the irreversibility of the connection between the metal element 25 and the connection element 16, the tang 26 can be embedded inside the polymeric material of the connection element 16.

According to another possible implementation of the irreversibility of the connection between the metal element 25 and the connection element 16a, represented for example in FIG. 4, the pointed element 12 can have, in the tang 26 of the metal element 25, the attachment element 23 substantially mating with the attachment part 22 of the connection end 16.

According to some embodiments, the pointed end 12 also comprises a fixing ring nut 27, for fixing the metal element 25 to the connection end 16 of the flexible stem 11.

According to some embodiments, the fixing ring nut 27 is made of polymeric material or metal material. For example, the polymeric material is preferably polyamide, but it can also be polyethylene, polypropylene or suchlike.

The fixing ring nut 27 can comprise a fixing element 28, mating with the fixing mean 24.

For example and with reference to FIG. 6, the fixing element 28 is a counter-thread. As a further example, the fixing element 28 can be a part suitable for an interlocking attachment.

According to some embodiments, the fixing element 28 can have an irreversible clamping position, for example a non-return interlocking attachment or a counter-thread with a gripping surface, or a serrated washer or suchlike.

According to some embodiments, the drill bit 10 comprises a gripping bushing 29, positioned sliding along the central axis of development X around the flexible stem 11, free to move between the attachment end 15 and the connection end 16 of the flexible stem 11.

Advantageously, the bushing 29 allows, in addition to directing the pointed end 12 in the work zone, to apply part of the force directly to a point closer to the work zone. In this case it can be used by pushing the pointed end 12 toward the work zone.

According to some embodiments, the bushing 29 has a hole in which the flexible stem 11 is inserted.

According to some embodiments, the edges 30 of the bushing 29 can have a greater thickness than the central body 31. Advantageously, a concavity is thus created that is able to accommodate the operator's fingers for a secure grip of the bushing 29 itself.

According to some embodiments, the edges 30 of the bushing 29 are rounded at least in their part 32 facing toward the flexible stem 11.

In this way, it is possible to prevent the bushing 29 from getting stuck against the flexible stem 11, when this is flexed during use. The bushing 29 can therefore remain free to move along the flexible stem 11 in any work condition whatsoever of the flexible stem 11.

Furthermore, it is possible to reduce the possibility of damaging the flexible stem 11 due to localized pressure points of the edge 30 of the bushing 29 on the flexible stem 11.

Some embodiments described here, as shown in FIGS. from 11 to 12, concern a support and guide device 50 for surgical drill bits.

Some embodiments described here, as shown in FIGS. from 7 to 10, also concern a surgical assembly 100 comprising a support and guide device 50 and a surgical drill bit 10 according to the invention. In particular, FIG. 10 shows the surgical assembly 100 during use in which the drill bit 10 is in a flexed configuration.

The support and guide device 50 has two arms 51, 52 pivoted to each other at an intermediate point O1.

Figure 8:
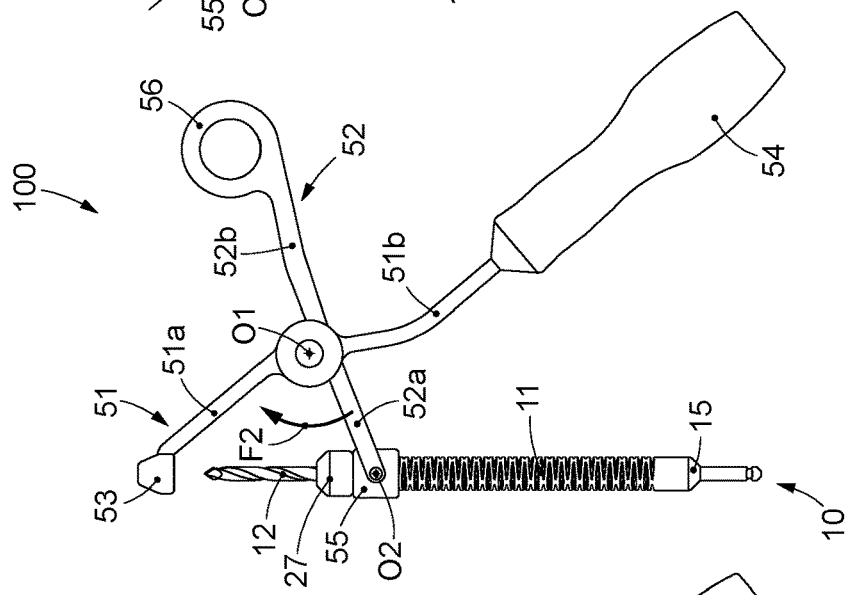

The support and guide device 50 can have two extreme positions, one completely divaricated (FIG. 11) and one closed (FIG. 12). The support and guide device 50 can also have all the positions comprised between the two extreme positions as above. The various positions can be assumed by moving the two arms 51, 52 one with respect to the other in rotation around the intermediate point O1 according to the movement indicated by the arrow F2 (FIGS. 8 and 11).

The intermediate point O1 can identify on each arm 51, 52 two respective half-arms 51a, 51b, 52a, 52b.

The half-arm 51a can comprise at the end opposite the intermediate point O1 a drill bit-clamping element 53.

The half-arm 51b can comprise at the end opposite the intermediate point O1 a manipulation handle 54.

The half-arm 52a can comprise at the end opposite the intermediate point O1 a bushing 55.

The half-arm 52b can comprise at the end opposite the intermediate point O1 a gripping element 56.

In a preferred embodiment and as shown in FIGS. from 7 to 12, the half-arm 52a has a shorter length than the half-arm 51a. For example, the ratio between the two half-arms 51a, 52a can be indicatively comprised between 0.4 and 0.8, preferably between 0.5 and 0.8, even more preferably between 0.6 and 0.8. Advantageously, when the support and guide device 50 cooperates during use with a surgical drill bit 10, in a closed position as shown for example in FIGS. 9 and 12, the manipulation handle is positioned according to an axis Y which has an angle smaller than 90° with respect to a central axis of development X of the drill bit 10, preferably smaller than 45°. In this way, it is possible to further increase the manageability of the drill bit 10.

The drill bit-clamping element 53 can be an element that has a through hole with a diameter greater than the pointed end 12 of the drill bit 10 and smaller than the external diameter of a clamping element of the drill bit 10.

The clamping element can have an external diameter greater than the pointed end 12 and a flexible stem 11 of the drill bit 10. In the attached drawings, the clamping element corresponds to a fixing ring nut 27 of the drill bit 10, however it can be an element different from the fixing ring nut 27 and able to be fixed on the flexible stem 11.

The bushing 55 can have a through hole with a diameter greater than the attachment end 15 and the flexible stem 11 of the drill bit 10 and smaller than the external diameter of the clamping element of the drill bit 10.

In a preferred but not exclusive embodiment, the drill bit 10 can have an attachment end 15 with a section that has sizes no greater than the diameter of the flexible stem, advantageously facilitating the insertion of the bushing 55. As a further advantage, in this case the bushing 55 can have a through hole with a diameter slightly greater than the diameter of the flexible stem 11, thus limiting the movement, or play, of the bushing 55 in a direction orthogonal to the central axis of development X.

Figure 7:
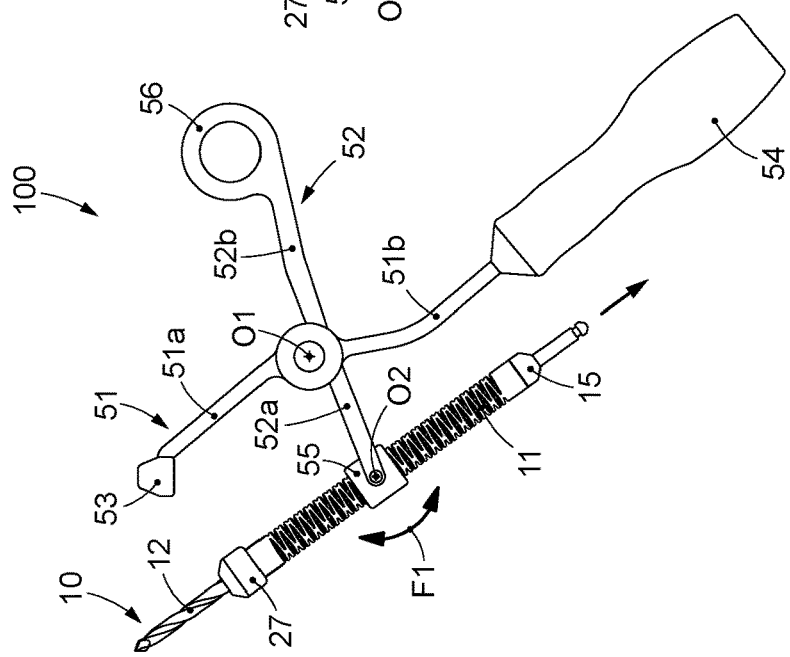

The bushing is pivoted on the end of the arm 52. In this way, the bushing 55 can be free to rotate according to the movement indicated by the arrow F1 in FIGS. 7 and 11.

The bushing can be able to slide along the flexible stem 11 of the drill bit 10.

The drill bit 10 can be inserted between the drill bit-clamping element 53 and the bushing 55. In a closed position of the support and guide device 50, the drill bit-clamping element 53 and the bushing 55 cooperate with the clamping element in order to clamp the drill bit 10.

The support and guide device 50 can therefore have a clamped position in which the bushing 55 and the drill bit-clamping element 53 cooperate with the drill bit 10, in order to keep it in a fixed position with respect to the support and guide device 50.

In a preferred embodiment, the manipulation handle 54 is a handle-shaped element (FIGS. from 7 to 12) able to be gripped by an operator. In alternative embodiments, it can be a gripping eyelet or other forms.

According to some embodiments, the gripping element 56 is a gripping eyelet (FIGS. from 7 to 12) or a gripping portion of a different shape.

The support and guide device 50 can also be applied to a surgical drill bit different from the present invention, if the surgical drill bit has an end for inserting the bushing 55 with sizes suitable for the end to pass in the through hole of the bushing 55. For example, the diameter of the end, or a larger diagonal in the case of a non-circular section or suchlike, has to be at least slightly smaller than the internal diameter of the bushing 55.

Some embodiments disclosed here also concern a method to produce a surgical drill bit 10 for a surgical tool or device.

According to some embodiments, the method provides to produce a flexible stem 11 completely in polymeric material provided with a proximal part and a distal part, wherein the distal part is made so as to define an attachment 13 for the rotational connection to said tool, and to couple a pointed end 12 to the proximal part.

According to some embodiments, the flexible stem 11 can be made by means of additive manufacturing technology, in particular by means of 3D rapid prototyping, or injection molding.

The method to produce the drill bit 10 can for example provide to:
 produce the flexible stem 11, made of polymeric material, and the attachment 13, in a single body or with subsequent fixing of the attachment 13 to the flexible stem 11;
 produce a fixing ring nut 27;
 fix the pointed end 12 onto the flexible stem 11, by means of the fixing ring nut 27.

According to some embodiments, the attachment 13 and the fixing ring nut 27 can be made of metal or polymeric material.

For example, if the attachment 13 and the fixing ring nut 27 are of polymeric material, they can be made by means of additive manufacturing technology, in particular by means of 3D rapid prototyping, or injection molding.

According to one embodiment, producing the drill bit 10 can comprise inserting the flexible stem 11 into a gripping bushing 29, before fixing the pointed end 12 onto the flexible stem 11.

According to one embodiment, the method to fix the pointed end 12 onto the flexible stem 11 comprises positioning a metal element 25 and fixing it on a connection end 16 of the flexible stem 11, in correspondence with the proximal part, by means of a fixing ring nut 27.

According to some embodiments and with reference to FIG. 5 and FIG. 6, fixing the metal element 25 provides in particular to insert the fixing ring nut 27 onto the metal element 25 up to the connection end 16 and to then fix the fixing ring nut 27 to the connection end 16.

For example, the fixing can be carried out by screwing the fixing ring nut 27 onto the connection end 16 until it grips, thus fixing it in an irreversible manner.

Some embodiments described here also concern a method to use a surgical assembly 100 according to the invention.

As shown in FIGS. from 7 to 10, the method can provide to:
 divaricate substantially completely a support and guide device 50;
 insert an attachment end 15 of a surgical drill bit 10 into a bushing 55 of the support and guide device 50 (FIG. 7);
 close the support and guide device 50 by making the bushing 55 slide on the surgical drill bit 10 until a pointed end 12 of the surgical drill bit 10 is inserted into a drill bit-clamping element 53 (FIG. 8);
 further close the support and guide device 50 by rotating the two arms 51, 52 one with respect to the other around the intermediate point O1 according to the movement indicated by the arrow F2 (FIG. 8), making the bushing 55 slide on the surgical drill bit 10 until the surgical drill bit 10 is clamped in a fixed position with respect to the support and guide device 50 (FIG. 9).

As shown in FIG. 10, the method further provides, during use, to move the drill bit 10 in the desired direction, flexing it by means of the support and guide device 11.

It is clear that modifications and/or additions of parts or steps may be made to the surgical drill bit 10, to the surgical assembly 100, to the support and guide device 50, to the method to produce a surgical drill bit 10 and to the method to use the surgical assembly 100 as described heretofore, without departing from the field of the present invention as defined by the claims.

It is also clear that, although the present invention has been described with reference to some specific examples, a person of skill in the art shall certainly be able to achieve many other equivalent forms of drill bit 10 and method, having the characteristics as set forth in the claims and hence all coming within the field of protection defined thereby.

In the following claims, the sole purpose of the references in brackets is to facilitate reading and they must not be considered as restrictive factors with regard to the field of protection claimed in the specific claims.

The invention claimed is:

1. A surgical drill bit able to be connected to a surgical tool, said drill bit comprising a flexible stem completely made of polymeric material and provided with a proximal part to which a pointed end is directly coupled and with a distal part which has an attachment for a rotational connection to said tool,
 wherein said flexible stem develops along a central axis (X) of development and comprises, in a single body, a flexible central part, disposed between said distal part and said proximal part, wherein said distal part comprises an attachment end which has said attachment and said proximal part has a connection end to which said pointed end is coupled,
 wherein said flexible central part has a three-dimensional reticular structure with meshes of polymeric material consisting of a repetition in space of meshes formed by bilobed elements, each bilobed element being connected to at least one contiguous bilobed element by at least two nodes, and
 wherein said at least two nodes which connect one bilobed element to at least one contiguous bilobed element are disposed substantially angularly opposite each other with respect to said central axis (X) of development.

2. The drill bit as in claim 1, wherein the at least two nodes reciprocally connecting said bilobed elements develop, along said central axis (X) of development, in accordance with an angularly offset angular development, wherein the at least two nodes that connect one bilobed element to at least one contiguous bilobed element are angularly offset with respect to at least another two nodes that connect another bilobed element to at least one contiguous bilobed element, along said central axis (X) of development.

3. The drill bit as in claim 2, wherein said nodes are angularly offset, by an angle comprised between 10° and 90° along said central axis (X) of development.

4. The drill bit as in claim 1, wherein said nodes act as predetermined breaking points of the flexible stem.

5. The drill bit as in claim 1, wherein said pointed end is connected to said proximal part of said flexible stem in a removable manner.

6. The drill bit as in claim 5, wherein said pointed end comprises a metal element connectable to said proximal part in an irreversible manner.

7. The drill bit as in claim 6, wherein said pointed end, also, comprises a fixing ring nut, for fixing the metal element to the connection end of the flexible stem.

8. The drill bit as in claim 1, said drill bit comprising a gripping bushing, positioned around the flexible stem sliding along said central axis (X) of development between the distal part and the proximal part of the flexible stem.

9. The drill bit as in claim 1, wherein said polymeric material is one of polyamide, polyethylene or polypropylene.

10. A surgical assembly comprising:
a surgical drill bit able to be connected to a surgical tool, said drill bit comprising a flexible stem completely made of polymeric material and provided with a proximal part to which a pointed end is directly coupled and with a distal part which has an attachment for a rotational connection to said tool; and
a support and guide device which has two arms pivoted to each other at an intermediate point (O1), one arm comprising at one end a manipulation handle and at an opposite end a drill bit-clamping element and the other arm comprising at one end a gripping element and at an opposite end a bushing, said bushing being pivoted on the opposite end of the other arm and able to slide along a flexible stem of said surgical drill bit.

11. A method to use a surgical assembly comprising:
a surgical drill bit able to be connected to a surgical tool, said drill bit comprising a flexible stem completely made of polymeric material and provided with a proximal part to which a pointed end is directly coupled and with a distal part which has an attachment for a rotational connection to said tool, and
a support and guide device which has two arms pivoted to each other at an intermediate point (O1), one arm comprising at one end a manipulation handle and at an opposite end a drill bit-clamping element and the other arm comprising at one end a gripping element and at an opposite end a bushing, said bushing being pivoted on the opposite end of the other arm and able to slide along said flexible stem of said surgical drill bit,
said method provides to:
divaricate the support and guide device in a substantially complete manner;
insert an attachment end of the surgical drill bit into the bushing of the support and guide device;
close the support and guide device by making the bushing slide on the surgical drill bit until the pointed end of the surgical drill bit is inserted into the drill bit clamping element; and
further close the support and guide device by making the bushing slide on the surgical drill bit until the surgical drill bit is clamped in a fixed position with respect to the support and guide device.

\* \* \* \* \*